(12) United States Patent
Kawamura et al.

(10) Patent No.: US 8,548,545 B2
(45) Date of Patent: Oct. 1, 2013

(54) METHOD FOR MEASURING A CONCENTRATION OF A BIOGENIC SUBSTANCE CONTAINED IN A LIVING BODY

(75) Inventors: Tatsurou Kawamura, Kyoto (JP); Masaru Minamiguchi, Kyoto (JP); Masahiko Shioi, Kyoto (JP)

(73) Assignee: Panasonic Corporation, Osaka (JP)

( * ) Notice: Subject to any disclaimer, the term of this patent is extended or adjusted under 35 U.S.C. 154(b) by 12 days.

(21) Appl. No.: 13/458,544

(22) Filed: Apr. 27, 2012

(65) Prior Publication Data

US 2012/0215078 A1  Aug. 23, 2012

Related U.S. Application Data

(63) Continuation of application No. PCT/JP2011/005515, filed on Sep. 29, 2011.

(30) Foreign Application Priority Data

Oct. 6, 2010  (JP) .................................. 2010-226327

(51) Int. Cl.
   *A61B 5/1455* (2006.01)
(52) U.S. Cl.
   USPC .......................................... 600/316; 600/310
(58) Field of Classification Search
   USPC ................................................. 600/310–344
   See application file for complete search history.

(56) References Cited

U.S. PATENT DOCUMENTS

| 2005/0027176 A1 | 2/2005 | Xie |
| 2008/0214913 A1 | 9/2008 | Van Gogh et al. |
| 2010/0087723 A1 | 4/2010 | Van Duyne et al. |
| 2010/0195106 A1 | 8/2010 | Ogawa |

FOREIGN PATENT DOCUMENTS

| JP | 2004-510527 | 4/2004 |
| JP | 2007-537805 | 12/2007 |
| JP | 2008-531989 | 8/2008 |
| JP | 2009-014380 | 1/2009 |
| WO | WO 02/30275 A1 | 4/2002 |
| WO | WO 2005/110207 A1 | 11/2005 |

OTHER PUBLICATIONS

Melissa F. Mrozek et al., "Detection and Identification of Aqueous Saccharides by Using Surface-Enhanced Raman Spectroscopy," Analytical Chemistry, vol. 74, No. 16, pp. 4069-4075, Aug. 15, 2002.
International Search Report issued in International Patent Application No. PCT/JP2011/005515, filed Sep. 29, 2011.

*Primary Examiner* — Eric Winakur
*Assistant Examiner* — Marjan Fardanesh
(74) *Attorney, Agent, or Firm* — McDermott Will & Emery LLP

(57) ABSTRACT

One of the purposes of the present invention is to provide a biogenic substance concentration measuring method with improved measuring accuracy. An embodiment of the present invention provides a method for measuring a concentration of a biogenic substance contained in a living body, the method comprises steps of preparing a measuring device, wherein the measuring device comprises a light source, an optical filter, and a light receiver; irradiating a substantially-parallel light from the light source onto a particle chip implanted in a skin though a position on the surface of the skin to generate a reflected light; inclining the light source and calculating the concentration of the biogenic substance on the basis of the difference of signals before and after the inclination.

5 Claims, 4 Drawing Sheets

METHOD FOR MEASURING A CONCENTRATION OF A BIOGENIC SUBSTANCE CONTAINED IN A LIVING BODY

RELATED APPLICATIONS

This application is a Continuation of International Application No. PCT/JP2011/005515, filed on Sep. 29, 2011, which in turn claims the benefit of Japanese Paten Application No. 2010-226327, filed on Oct. 6, 2010, the disclosures of which Applications are incorporated by reference herein.

TECHNICAL FIELD

This invention relates to a method for measuring a concentration of a biogenic substance such as glucose contained in a living body.

BACKGROUND ART

A concentration of a biogenic substance such as glucose contained in a living body is measured on the basis of reflected light, scattered light, or transmitted light of light irradiated on the living body. More specifically, Raman scattering light of the biogenic substance is observed, and the concentration of the biogenic substance is calculated on the basis of the intensity of the Raman scattering light.

Patent Literature 1 and 2 disclose a method for measuring a glucose concentration optically. According to the method, first, a particle is implanted in the upper layer of a skin. The particle contains a reagent to react with glucose and to change a fluorescence property thereof. Next, the particle is irradiated with light having an exciting wavelength from the outside of the living body so as to measure fluorescence generated at the particle through the skin. On the basis of the measured fluorescence, the glucose concentration is measured.

[CITATION LIST]
[Patent Literature]
[PTL 1]
Japanese Unexamined Patent Application Publication (Translation of PCT Application) No. 2004-510527.
[PTL 2]
Japanese Unexamined Patent Application Publication (Translation of PCT Application) No. 2007-537805.
[Non-Patent Literature]
[NPL 1]
Melissa F. Mrozek, and Michael J. Weaver, "Detection and Identification of Aqueous Saccharides by Using Surface-Enhanced Raman Spectroscopy", Analytical Chemistry, Vol. 74, No. 16, 4069-4075, 2002

SUMMARY OF INVENTION

Technical Problem

One of the purposes of the present invention is to provide a method for more accurately measuring a concentration of a biogenic substance contained in a living body.

Solution to Problem

To solve the above problem, the illustrative embodiments of the present invention are provided as follows:

[1] A method for measuring a concentration of a biogenic substance contained in a living body, the method comprising steps of:
a step (a) of preparing a measuring device, wherein the measuring device comprises a light source, an optical filter, and a light receiver,
a step (b) of irradiating a substantially-parallel light from the light source onto a particle chip implanted in a skin though a position on the surface of the skin to generate a first reflected light, wherein the particle chip comprises a substrate and a plurality of metal particles,
a step (c) of receiving the first reflected light by the light receiver through the optical filter to obtain a first signal Xa, wherein the following equation is satisfied:

$$\text{lambda}_2 = (10^7 * \text{lambda}_1)/(10^7 - B * \text{lambda}_1) \quad\quad\quad (III).$$

$\text{lambda}_2$: wavelength of the light which penetrates the filter
$\text{lambda}_1$: wavelength of the substantially-parallel light
B: Raman shift proper to the biogenic substance
a step (d) of inclining the light source,
a step (e) of irradiating the position identical to said position with the substantially-parallel light in such a manner that the particle chip is not irradiated with the substantially-parallel light so as to obtain a second reflected light,
a step (f) of receiving the second reflected light by the light receiver through the optical filter to obtain a second signal Xb, and
a step (g) of calculating the concentration of the biogenic substance on the basis of the difference between the first signal Xa and the second signal Xb.

The method according to item 1, wherein the biogenic substance is glucose, and B is 1120 $\text{cm}^{-1}$.

The method according to item 1, wherein the step (b) and step (c) are performed at the same time.

The method according to item 1, wherein the step (d) and step (e) are performed at the same time.

The method according to item 1, wherein the step (d) to step (f) are performed at the same time.

Advantageous Effect of Invention

An embodiment of the present invention provides a method for more accurately measuring a concentration of a biogenic substance contained in a living body.

DESCRIPTION OF EMBODIMENTS

Figure 1:
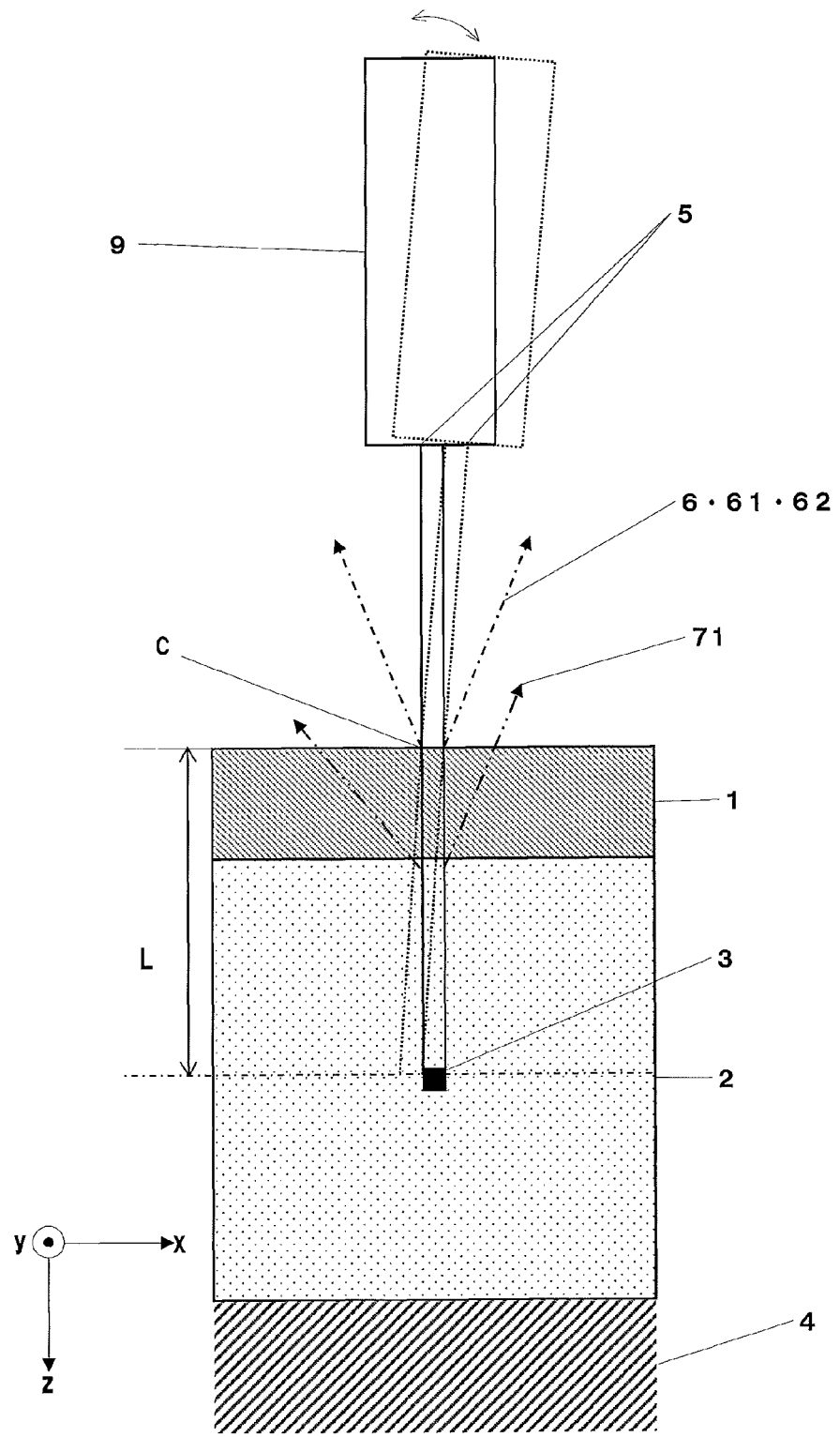
FIG. 1 shows a cross-sectional view of the skin.
Figure 3:
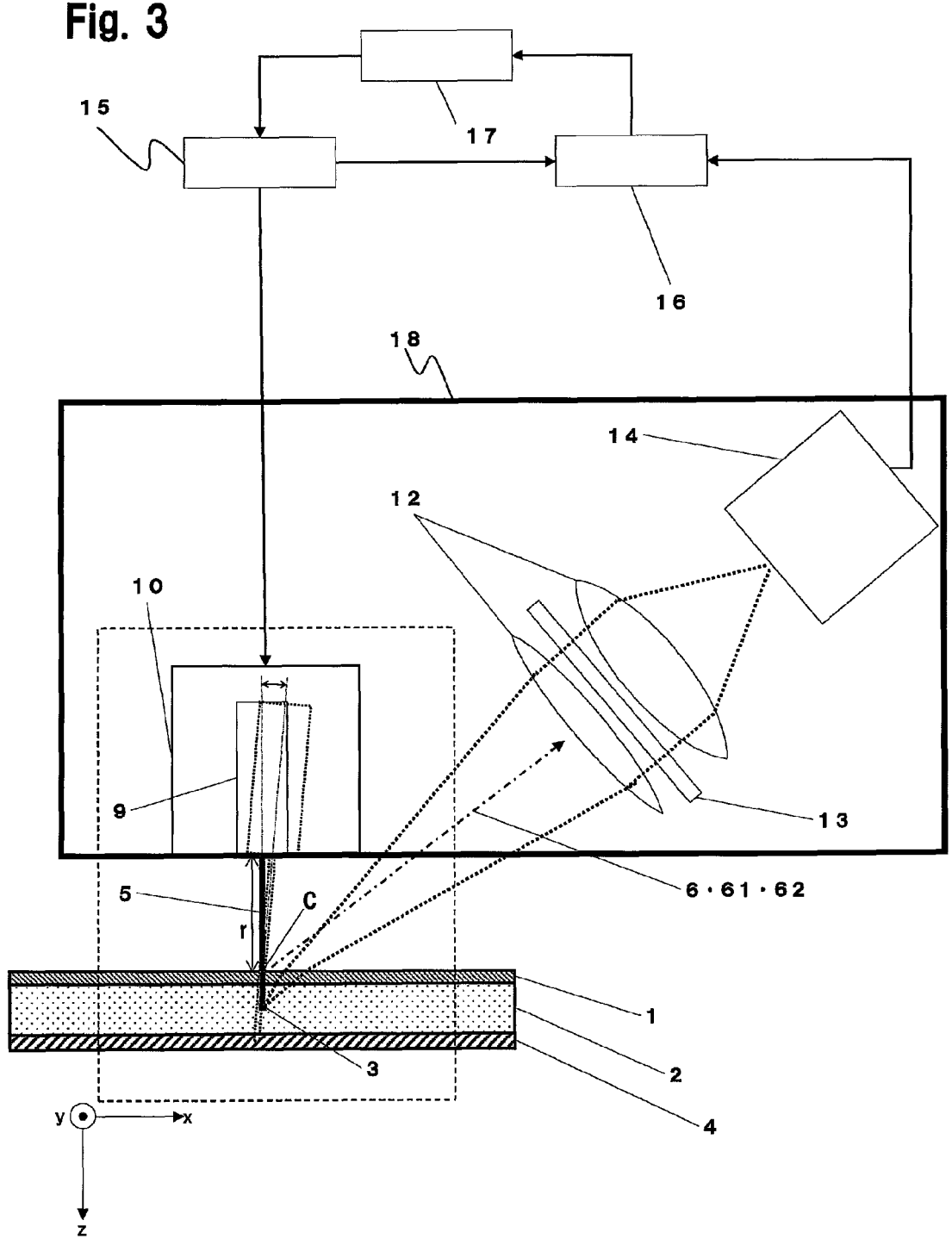
FIG. 3 shows a measuring device.

[Embodiment 1]
A method for measuring a concentration of a biogenic substance according to an illustrative embodiment (Embodiment 1) is described with reference to the drawings. The components in the drawings are not necessarily to scale, emphasis instead being placed upon clearly illustrating the principles of the present invention. In this embodiment, a method is provided for measuring a concentration of a biogenic substance contained in a living body. The method comprises steps described in the following paragraphs:

(Step (a))
In the step (a), the measuring device is prepared. As shown in FIG. 3, the measuring device comprises a light source 9, an optical filter 13, and a light receiver 14. The measuring device optionally comprises a light path modulator 10, a lens system 12, a signal generator 15, a lock-in amplifier 16, and a computer 17.

The signal generator 15 supplies a modulation signal to vary the light path and the condition of irradiation to the light-path modulator 10. The lock-in amplifier 16 uses the modulation signal as a reference signal to perform phase detection of the output signal from the light receiver 14. The computer 17 calculates a concentration of the biogenic substance on the basis of the output signal of the lock-in amplifier 16. The computer 17 also controls the signal generator 15. The support 18 holds the light-path modulator 10, the lens system 12, the filter 13, and the light receiver 14.

(Steps (b) and (c))

FIG. 1 shows an exploded cross-sectional view of the skin surrounded by the dashed line in FIG. 3. In the step (b), as shown in FIGS. 1 and 3, the light from the light source 9 penetrates the position C, which is located at the skin surface. A particle chip 3 implanted in a skin is irradiated with the light which has penetrated so as to generate a first reflected light 6 there.

In the step (c), as shown in FIG. 1, the first reflected light 6 is refracted at the skin surface due to the difference between the refraction index of the skin (approximately 1.37) and that of air (1). Then, as shown in FIG. 3, the refracted first reflected light 6 penetrates the optical filter 13 and is received by the light receiver 14. Thus, a first signal Xa is obtained.

The steps (b) and (c) are preferably performed at the same time.

As shown in FIG. 1, the skin comprises an epidermal tissue 1, a dermal tissue 2, and a hypodermal tissue 4. The epidermal tissue 1, the dermal tissue 2, and the hypodermal tissue 4 are stacked in this order.

An epidermal tissue 1 is located at the surface of the living body. The epidermal tissue 1 has a thickness of approximately 0.2 millimeters to 0.5 millimeters. A dermal tissue 2 has a thickness of approximately 0.5 millimeters to 2 millimeters. A particle chip 3 is implanted in the dermal tissue 2 and maintained while the particle chip 3 is immersed in an interstitial fluid, which is a living fluid between tissue cells. The hypodermal tissue 4 is constituted mainly of adipose tissue.

The term "body fluid" used in the present specification means an interstitial fluid.

Because the dermal tissue 2 has a plurality of blood capillaries, the body fluid contains biogenic substances in the blood capillaries. In particular, since a blood capillary wall is highly permeable to glucose, glucose concentration in the body fluid has high correlativity with blood sugar level.

The light source 9 emits a substantially-parallel light 5 to the skin along the Z-direction in FIG. 1. An example of the substantially-parallel light 5 is a light having a wavelength of 785 nanometers and having shape of circular beam with a diameter of 100 micrometers. The substantially-parallel light 5 penetrates the epidermal tissue 1 to travel onto the particle chip 3. The substantially-parallel light 5 is reflected on the particle chip 3 to generate a first reflected light there.

Figure 2:
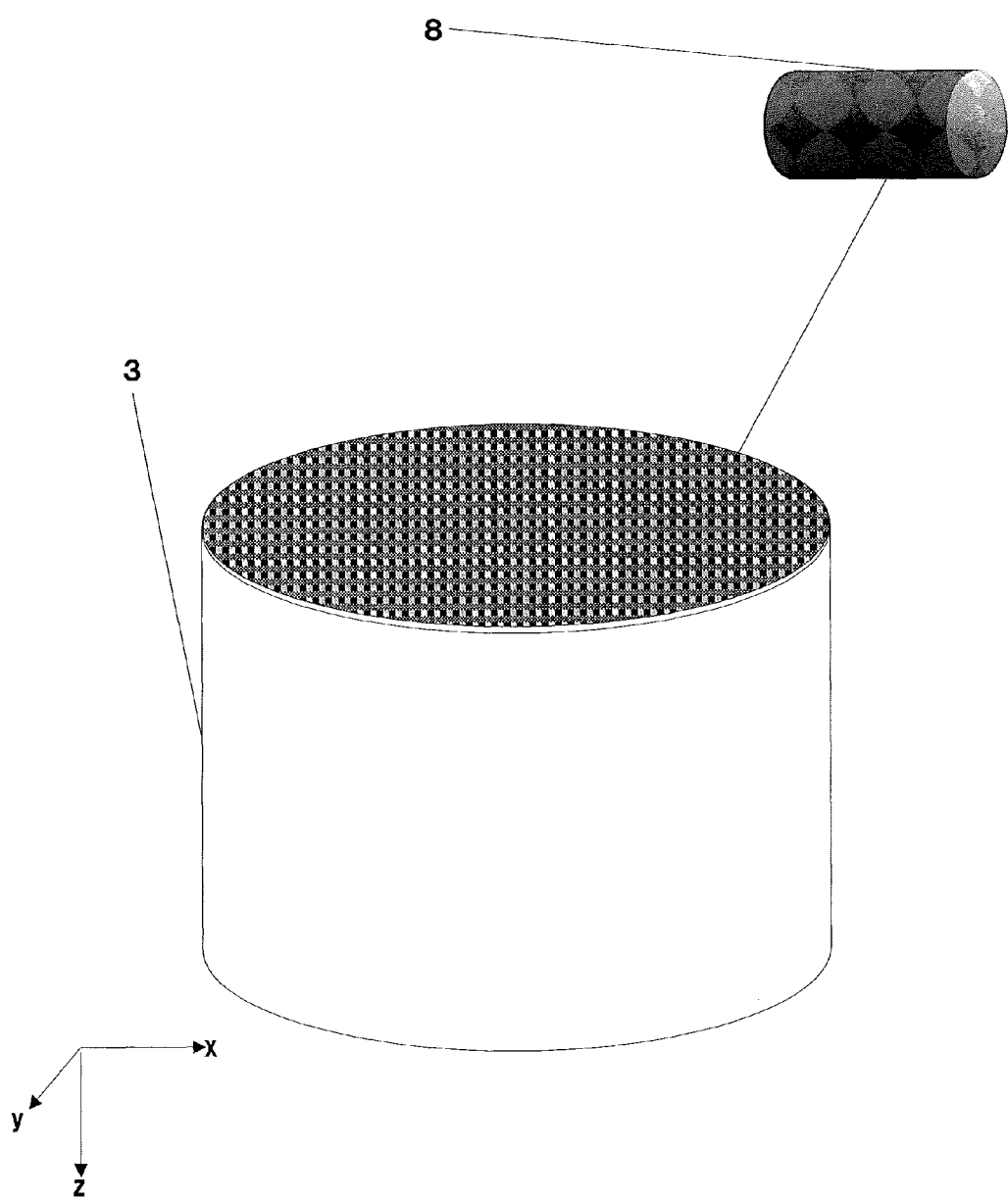
FIG. 2 shows a particle chip 3.

FIG. 2 shows a particle chip 3. The particle chip 3 comprises a substrate and metal particles 8 disposed on the surface of the substrate. An example of the number of the metal particles 8 is approximately 10,000. The metal particle 8 is irradiated with light to generate localized surface Plasmon resonance. One example of the particles 8 is a gold nano-rod having a diameter of approximately 10 nanometers and a length of 38 nanometers. Instead of the gold nano-rods, dielectric particles each having a surface coated by the metal such as gold or silver may be used. An example of the dielectric particles is silica.

The metal particle 8 has localized surface Plasmon resonance wavelength of 785 nanometers. The particle 8 has half bandwidth of approximately 70 nanometers. The term "localized surface plasmon resonance wavelength"" used in the present specification means the peak wavelength of absorption of light.

The substrate has a diameter of approximately 100 micrometers and a thickness of 100 micrometers. An example of the material of the substrate is resin such as acrylic resin, glass, or silicon. The particles 8 are disposed in such a manner that respective longitudinal axes directions are parallel to X-direction. Y-direction is orthogonal to the X-direction in the surface of the substrate. Z-direction is a direction along the thickness of the substrate. US Pre-Grant Patent application Publication No. 2010/0195106 discloses the particle chip 3 in more detail. US Pre-Grant Patent application Publication No. 2010/0195106 corresponds to W02007/108453 and Japanese patent laid-open publication No. 2007-248284.

As shown in FIG. 1, the particle chip 3 is implanted in the dermal tissue 2 so that the plane which comprises the particles 8 is parallel to the epidermal tissue 1. The distance L from the epidermal tissue 1 to the particle chip 3 is approximately 1.5 millimeters.

When the particle chip 3 is irradiated with the substantially-parallel light 5, the localized surface plasmon resonance is generated to increase electromagnetic field strength on the periphery of the particles 8. This enhances the Raman scattering light from the biogenic substance located on the periphery (not more than 0.5 to 30 nanometers) of the particles 8. Thus, surface-enhanced Raman scattering light is generated. The first reflected light 6 includes the surface-enhanced Raman scattering light.

The intensity of the surface-enhanced Raman scattering light is $10^4$ to $10^9$ times greater than the intensity of normal Raman scattering light. Accordingly, the surface-enhanced Raman scattering light generated on the periphery of the particles 8 has significantly greater intensity than the Raman scattering light generated in the skin surface (including the cuticle), in the epidermal tissue 1, or in the dermal tissue 2. This means that the Raman scattering light derived from a biogenic substance contained in a body fluid on the periphery of the particles 8 is selectively enhanced. Thus, the influence of the stray light and the interruption component is lowered.

The amount of the biogenic substance such as glucose contained in a living body is significantly lower than the amount of the interruption component contained in the living body. Accordingly, normal Raman scattering light of glucose has significantly smaller intensity than the Raman scattering light of the interruption component contained in the skin surface (including the cuticle), in the epidermal tissue 1, or in the dermal tissue 2. For this reason, it is hard to extract the normal Raman scattering light of glucose.

However, the particle chip 3 selectively enhances the Raman scattering light of glucose contained in a body fluid of the dermal tissue 2. This increases the intensity of the Raman scattering light of glucose selectively, compared to the intensity of the Raman scattering light of the interruption substance. Since the intensity of the surface-enhanced Raman scattering light of glucose is proportional to the concentration of the glucose, the concentration of glucose is calculated from the intensity of the surface-enhanced Raman scattering light of the glucose.

An example of calculating a concentration of glucose is described below.

FIG. 1 of non-Patent Literature 1 shows the surface-enhanced Raman scattering light spectrum of glucose. The surface-enhanced Raman scattering light of glucose has a plurality of peaks specific to glucose in the Raman shift range of 1000 to 1500 cm$^{-1}$.

Out of the plurality of peaks, the peak having a Raman shift of 1120 cm$^{-1}$ does not overlap the peaks of the Raman scattering light spectra of albumin and creatinine. Accordingly, the intensity of the surface-enhanced Raman scattering light having the Raman shift of 1120 cm$^{-1}$ is proportional only to the concentration of glucose.

When the wavelength of the substantially-parallel light 5 is 785 nanometers, a filter which light having a wavelength of 860.7 nanometers penetrates is used as the optical filter 13. The reason thereof is described below.

The relationship between wavelength lambda and wave number k satisfies the following equation (I):

$$k(\text{cm}^{-1}) = 10^7/\text{lambda (nanometer)} \tag{I}$$

The wavelength of 785 nanometers corresponds to a wave number of 12,739 cm$^{-1}$. Accordingly, the wave number of the Raman scattering light specific to glucose with a Raman shift of 1120 cm$^{-1}$ is calculated by the following equation.

$$12739(\text{cm}^{-1}) - 1120(\text{cm}^{-1}) = 11619(\text{cm}^{-1}).$$

When converted according to the equation (I), the wavelength of the Raman scattering light specific to glucose, which has a Raman shift of 1120 cm$^{-1}$ is 860.7 nanometers.

For example, the optical filter 13 has a central wavelength of 860.7 nanometers and a full width at half maximum of 3 nanometers. The penetration range of the optical filter 13 is 859.2 nanometers to 862.2 nanometers. According to the equation (I), the wave number of the penetration range is 11,599 cm$^{-1}$ to 11,639 cm$^{-1}$.

Figure 4:
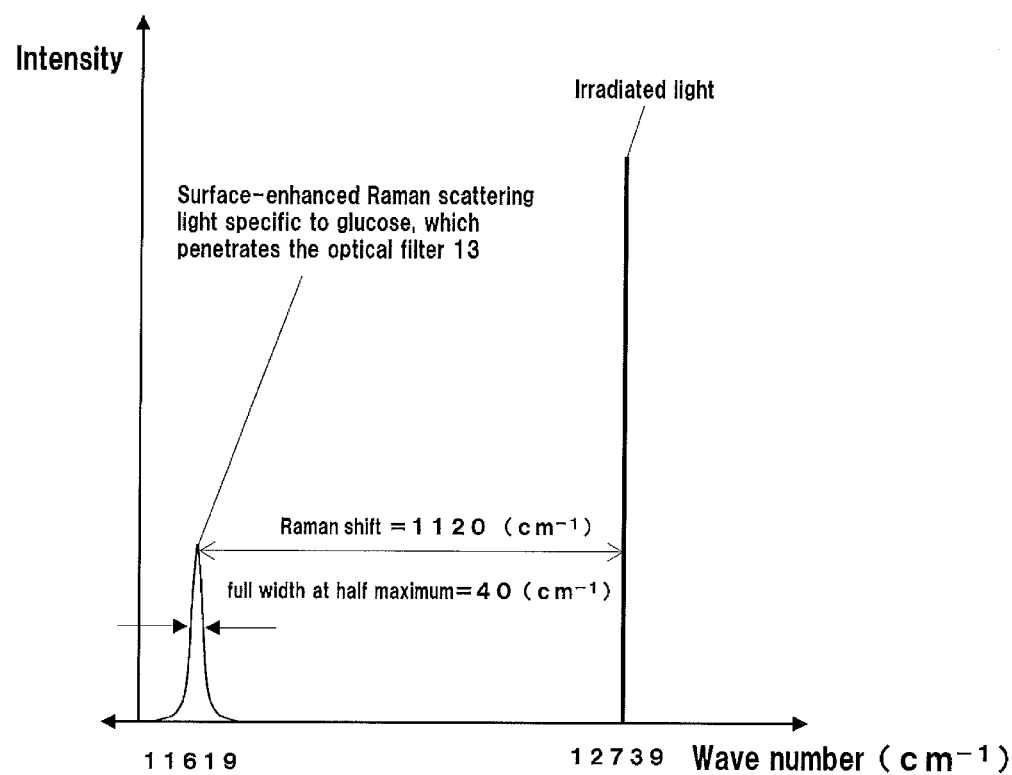
FIG. 4 shows a surface-enhanced Raman scattering light.

FIG. 4 shows the relationships among the irradiated light, the surface-enhanced Raman scattering light, the Raman shift, and the full width at half maximum.

The central wavelength and width of the surface-enhanced Raman scattering light spectrum specific to glucose fall within the acceptable range for transmission, which is defined by the central wavelength and width of the penetration spectrum of the optical filter 13. Because of this setting, the surface-enhanced Raman scattering light specific to glucose penetrates the optical filter 13. However, other lights fail to penetrate the optical filter 13.

In more detail, as shown in FIG. 4, only the Raman scattering light having a Raman shift value ranging from 1100 cm$^{-1}$ to 1140 cm$^{-1}$ with regard to the first focused light 5a, which has a wave number of 12,739 cm$^{-1}$, penetrates the optical filter 13 selectively. On the other hand, the optical filter 13 selectively restricts transmission of unwanted wavelengths of light, which includes the Raman scattering light of the interruption component and the first reflected light 6. The wave number of the Raman shift light having a Raman shift of 1100 cm$^{-1}$ is 11,639 cm$^{-1}$ (12,739 cm$^{-1}$ – 1,100 cm$^{-1}$ = 11,639 cm$^{-1}$), and the wave number of the Raman shift light having a Raman shift of 1140 cm$^{-1}$ is 11,599 cm$^{-1}$ (12,739 cm$^{-1}$ – 140 cm$^{-1}$ = 11,599 cm$^{-1}$). These values correspond with the wave numbers of the end points of the penetration range of the optical filter 13.

If the intensity of the first focused light 5a is enhanced in order to enhance the intensity of the surface enhanced Raman scattered light, the intensity of the reflected light 6 and the intensity of the Raman scattered light of interruption components are also enhanced. However, the Raman scattered light of the interruption components and the reflected light 6 are shielded by the optical filter 13, and do not reach the light sensor 14. Thus, only the first signal Xa specific to the target substance is obtained.

The central wavelength lambda$_2$ of the optical filter 13 used for measuring a glucose concentration is calculated by the following formula (II). Lambda$_1$ represents a wavelength of the first focused light 5a.

$$\text{lambda}_2 = (10^7 * \text{lambda}_1)/(10^7 - 1120 * \text{lambda}_1) \tag{II}$$

lambda$_2$: the central wavelength of the optical filter 13
lambda$_1$: the wavelength of the first focused light 5a As described above, the measuring device is used to selectively measure the surface-enhanced Raman scattering light of glucose, which has the Raman shift of 1120 cm$^{-1}$.

Needless to say, similarly to a case of a typical measurement, a standard curve prepared beforehand is used on the above-mentioned measurement.

Instead of the equation (II), the following equation (III) is employed to calculate a concentration of a biogenic substance having a Raman shift of B cm$^{-1}$.

$$\text{lambda}_2 = (10^7 * \text{lambda}_1)/(10^7 - B * \text{lambda}_1) \tag{III}$$

lambda$_2$: the central wavelength of the optical filter 13
lambda$_1$: the wavelength of the first focused light 5a
B: Raman shift of the biogenic substance
(Steps (d) to (f))

Seemingly, the concentration of the biogenic substance appears to be measured through the steps (a) to (c). However, the obtained value of the concentration is inaccurate. The reason is described below.

The first reflected stray light 61 includes stray light. The stray light lowers the measurement accuracy. The stray light includes a reflected stray light 61 and the diffused and scattered light 71. The reflected stray light 61 is generated from the skin surface by irradiating the skin surface with the substantially-parallel light 5. The diffused and scattered light 71 is generated from the inside of the skin by the substantially-parallel light 5 travelling inside of the skin.

The reflected stray light 61 lowers the measurement accuracy greatly, whereas the diffused and scattered light 71 hardly lowers the measurement accuracy. This is because the intensity of the reflected stray light 61 is much greater than the intensity of the diffused and scattered light 71.

The larger the difference of the refractive index is, the greater the amount of the reflected stray light 61 is. The substantially-parallel light 5 travels from the air to the inside of the skin. Due to the great difference, which is approximately 0.37, between the refractive index of the air and the refractive index of the skin, the substantially-parallel light 5 is largely reflected at the skin surface.

On the other hand, since the refractive index inside the skin is substantially constant, the intensity of the diffused and scattered light 71 is much weaker than that of the reflected stray light 61 (approximately 1.37).

The substantially-parallel light 5 is reflected strongly to all directions on the skin surface to generate the reflected stray light 61. The reflected stray light 61 is generated at the cuticle, which has a thickness of 10 to 20 micrometers), and is located at the top of a skin. The intensity of the reflected stray light 61 is equal to approximately four to seven percent of the intensity of the irradiated light. The intensity of the reflected stray light 61 varies depending on the surface roughness of the cuticle and on the distribution of the regions with different refractive index.

On the other hand, the intensity of normal Raman scattering light is not more than 10$^{-16}$ times of the intensity of the irradiated light. The intensity of the surface-enhanced Raman scattering light is not more than $10^{-7}$ times of the intensity of the irradiated light. In other words, the intensity of the reflected stray light 61 generated on the skin surface is significantly greater than that of the surface-enhanced Raman scattering light, which should be detected. Accordingly, even if the intensity of the reflected stray light 61 is significantly small, incorporation of the reflected stray light 61 into a light receiver 14 saturates the output signal of the light receiver 14 and causes the measurement to be impossible.

The optical filter 13 may decrease the amount of the first reflected stray light 61 incorporating into the light receiver 14 and may prevent the light sensor 14 from being saturated.

However, when the transmittance of the light penetrating the optical filter 13 is decreased (namely, when the shielding effect of the optical filter 13 is increased), the transmittance of the Raman scattering light is also decreased. Practically, the minimum value of the transmittance of the light penetrating the optical filter 13 is approximately $10^{-8}$. In other words, all the reflected stray light 61 is not shielded, and some of the reflected stray light 61 penetrates the optical filter 13. The some of the reflected stray light 61 incorporates into the light receiver 14, and lowers the measurement accuracy of the concentration of the biogenic substance.

Furthermore, living bodies have substances having a Raman spectrum which overlaps the Raman spectrum of the biogenic substance such as glucose. Even if the optical filter 13 is used, the Raman scattering light (hereinafter, "the interruption Raman light") generated by the substances fails to be decreased. This also lowers the measurement accuracy of the concentration of the biogenic substance.

In order to solve the above-mentioned problem, the steps (d) to (f) are performed in this embodiment of the present invention. It is preferred that the steps (d) and (e) are performed at the same time. It is more preferred that the steps (d) to (f) are performed at the same time.

(Step (d))

First, in the step (d), the light source 9 is inclined. An example of the inclination angle of the light source 9 is not less than 3 degrees and not greater than 20 degrees.

(Step (e))

In the step (e), the substantially-parallel light 5 penetrates the position C. As shown in FIG. 1, since the light source 9 is inclined, the particle chip 3 fails to be irradiated with the substantially-parallel light 5 which has penetrated the position C.

In the step (e), it is required that the substantially-parallel light 5 penetrates the position C. In other words, a position on the skin surface other than position C must not be irradiated with the substantially-parallel light 5. The reason is described below.

Optical characteristic depends on surface roughness, distribution of the refractive index, and the concentration of the interruption component. The optical characteristic is not uniform even in a single individual. In other words, the optical characteristic varies depending on the position on the skin surface.

Accordingly, even if a single individual is irradiated with the light having identical intensity, the intensity of the reflected stray light 61 varies on the position which is irradiated with the light. Therefore, in the step (e), the substantially-parallel light 5 is required to penetrate the position C.

Similarly to the case of the step (b), the reflected stray light 61 also is generated in the step (e). The reflected stray light generated in the step (e) is referred to as the second reflected stray light 62. Needless to say, the second reflected stray light 62 fails to include the surface-enhanced Raman scattering light, since the light source 9 is inclined.

Similarly to the case of the step (c), in the step (f), the second reflected stray light 62 is received by the light receiver 14 through the optical filter 13 to obtain a second signal Xb. Finally, in the step (g), the second signal Xb is deducted from the first signal Xa to calculate the difference therebetween. The concentration of the biogenic substance is calculated on the basis of the difference. The computer 17 calculates these.

The deduction of the second signal Xb from the first signal Xa cancels the reflected stray light 61, which lowers the measurement accuracy greatly. The interruption Raman light is also cancelled. In other words, the difference includes the component of neither the reflected stray light 61 nor the interruption Raman light. Accordingly, the concentration obtained through the steps (a) to (f) is more accurate than the concentration obtained through only the steps (a) to (c).

INDUSTRIAL APPLICABILITY

An embodiment of the present invention can be employed to measure a concentration of a substance such as glucose in a living body.

Referential Signs List
1: epidermal tissue
2: dermal tissue
3: particle chip
4: hypodermal tissue
5: substantially-parallel light
6: reflected light
71: diffused and scattered light
8: metal particle
9: light source
10: light-path modulator
12: lens system
13: optical filter
14: light receiver
15: signal generator
16: lock-in amplifier
17: computer
18: support

The invention claimed is:

1. A method for measuring a concentration of a biogenic substance contained in a living body, the method comprising steps of:

a step (a) of preparing a measuring device, wherein the measuring device comprises a light source, an optical filter, and a light receiver, a step (b) of irradiating a substantially-parallel light from the light source onto a particle chip implanted in a skin though a position on the surface of the skin to generate a first reflected light, wherein the particle chip comprises a substrate and a plurality of metal particles, a step (c) of receiving the first reflected light by the light receiver through the optical filter to obtain a first signal Xa, wherein the following equation is satisfied:

$$\text{lambda}_2 = (10^7 * \text{lambda}_1)/(10^7 - B * \text{lambda}_1) \qquad (III)$$

lambda$_2$: wavelength of the light which penetrates the filter
lambda$_1$: wavelength of the substantially-parallel light
B: Raman shift proper to the biogenic substance a step (d) of inclining the light source,
a step (e) of irradiating the position identical to said position with the substantially-parallel light in such a manner that the particle chip is not irradiated with the substantially-parallel light so as to obtain a second reflected light, a step (f) of receiving the second reflected light by the light receiver through the optical filter to obtain a second signal Xb, and a step (g) of calculating the concentration of the biogenic substance on the basis of the difference between the first signal Xa and the second signal Xb.

2. The method according to claim 1, wherein
the biogenic substance is glucose, and
B is $1120\ cm^{-1}$.

3. The method according to claim 1, wherein
the step (b) and step (c) are performed at the same time.

4. The method according to claim 1, wherein
the step (d) and step (e) are performed at the same time.

5. The method according to claim 1, wherein
the step (d) to step (f) are performed at the same time.

\* \* \* \* \*